US007776023B2

(12) United States Patent
Hatayama

(10) Patent No.: US 7,776,023 B2
(45) Date of Patent: Aug. 17, 2010

(54) METHOD AND IMPLEMENT FOR OPENING HOLE IN SOFT MATERIAL

(75) Inventor: Yutaka Hatayama, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 12/364,989

(22) Filed: Feb. 3, 2009

(65) Prior Publication Data

US 2009/0171246 A1 Jul. 2, 2009

Related U.S. Application Data

(63) Continuation of application No. 10/862,465, filed on Jun. 8, 2004, now abandoned, which is a continuation of application No. PCT/JP02/03743, filed on Apr. 15, 2002.

(30) Foreign Application Priority Data

Dec. 12, 2001 (JP) ............................ 2001-378266

(51) Int. Cl.
*A61B 19/00* (2006.01)
*A61M 5/32* (2006.01)

(52) U.S. Cl. ....................... 604/411; 600/573; 600/576; 600/579

(58) Field of Classification Search ................. 600/573, 600/576–579; 604/274, 403, 411–414
See application file for complete search history.

(56) References Cited

U.S. PATENT DOCUMENTS 2,560,162 A 7/1951 Ferguson
2,716,983 A 9/1955 Windischman et al.
2,717,600 A 9/1955 Huber
3,064,651 A 11/1962 Henderson
3,071,135 A 1/1963 Baldwin et al.
3,119,391 A 1/1964 Harrison
3,906,932 A 9/1975 Ayres
3,924,617 A 12/1975 Ferro (Continued)

FOREIGN PATENT DOCUMENTS

JP 54-017587 2/1979

(Continued)

*Primary Examiner*—Max Hindenburg
*Assistant Examiner*—Rene Towa
(74) *Attorney, Agent, or Firm*—Sterne, Kessler, Goldstein & Fox P.L.L.C.

(57) ABSTRACT

An hole-opening implement (5 or 50) for opening a hole in a soft material (2) has a first cutting part and a second cutting part. To pierce the soft material with the hole-opening implement, both cutting parts advances in the soft material while cutting the soft material. Such a state that the second cutting part remains in the soft material just after the first cutting part is passed through the soft material is assured so that a cut piece as bound to the soft material can remain after the opening. The first cutting part is formed at a tip of the hole-opening implement, and the second cutting part is disposed behind the first cutting part in the piercing direction of the hole-opening implement. Otherwise, the hole-opening implement may be constructed so that the first cutting part is sharp in section and the second cutting part is formed so as to have lower cutting force than the first cutting part.

4 Claims, 8 Drawing Sheets

U.S. PATENT DOCUMENTS

| | | | | |
|---|---|---|---|---|
| 4,020,837 | A | 5/1977 | Larson | |
| 4,935,020 | A | 6/1990 | Broden | |
| 4,951,512 | A * | 8/1990 | Mazza et al. | 73/864.23 |
| 5,020,220 | A * | 6/1991 | Miyake et al. | 30/2 |
| 5,354,537 | A | 10/1994 | Moreno | |
| 5,456,887 | A | 10/1995 | Calvo et al. | |
| 5,733,266 | A * | 3/1998 | Gravlee, Jr. | 604/272 |
| 5,807,277 | A * | 9/1998 | Swaim | 600/567 |
| 6,280,400 | B1 | 8/2001 | Niermann | |
| 6,562,300 | B2 | 5/2003 | Rosen et al. | |
| 6,626,887 | B1 | 9/2003 | Wu | |
| 2002/0042581 | A1 | 4/2002 | Cervi | |
| 2002/0052619 | A1 * | 5/2002 | Transue | 606/185 |
| 2002/0141904 | A1 | 10/2002 | Rosen et al. | |

FOREIGN PATENT DOCUMENTS

| | | |
|---|---|---|
| JP | 5-39508 | 5/1993 |
| JP | 09-131336 | 5/1997 |
| JP | 10-201742 | 8/1998 |
| JP | 10-274656 | 10/1998 |

* cited by examiner

METHOD AND IMPLEMENT FOR OPENING HOLE IN SOFT MATERIAL

REFERENCE TO RELATED APPLICATION

This application is a Continuation of U.S. application Ser. No. 10/862,465, filed Jun. 8, 2004, which is a continuation application of PCT/JP02/003743 filed Apr. 15, 2002, each of which is hereby incorporated in its entirety herein by reference thereto.

BACKGROUND OF THE INVENTION

1. Field of the Invention

The present invention relates to a method and implement for opening a hole in soft material such as rubber, synthetic rubber and synthetic resin.

2. Background Art

Conventionally, as disclosed in the Japanese Patent Laid Open Gazette Hei. 10-274656, there is a well-known device for fully automatically measuring glucose by measurement of whole blood specimen. Also, there is well known an art disclosed in the Japanese Patent Laid Open Gazette Hei. 10-201742 and an art disclosed in the Japanese Patent Laid Open Gazette Hei. 9-131336 as arts of a vacuum blood-collection tube for collecting specimen of blood.

The vacuum blood-collection tube is sealed with a plug made of soft material, such as rubber, so as to keep vacuum state therein. Accordingly, when blood gathered by the vacuum blood-collection tube is sampled to an analysis device automatically, a suction nozzle for sucking blood is brought into the vacuum blood-collection tube. By making diameter of the suction nozzle large, suction time becomes short, whereby time required for one process of analysis can be shorten so much. However, it is required to open a hole of large diameter on the plug so as to make the suction nozzle of so large diameter pass therethrough. As a mean for opening such the hole, conventionally, a method of rotating the nozzle like a drill so as to open a hole, or a punching method that an open-end stick such as a needle (an open-end pipe or the like) is pressed against the plug and pressure is applied thereto so as to penetrate the plug.

However, in the case of boring like a drill, small refuses of soft material disperse and are sucked into the suction nozzle together with blood. On the other hand, in the case of the punching method, a pillar-shaped cut piece of soft material (punched refuse) is separated from the plug and sucked to a tip of the suction nozzle for sampling, whereby the cut piece is conveyed to a blood passage of the analysis device. The punched refuse and the small refuses contaminated in blood are analyzed as foreign substance in analysis route, thereby reducing analysis accuracy. Also, in the blood passage, the punched refuse and the small refuses may be caught in an on-off solenoid valve serving as a volume determination mean for passing a fixed volume, thereby preventing normal opening/closing of the on-off solenoid valve. For preventing this fault, it is required to interpose a filter for removing the punched refuse and the like in a sampling blood supply route, and the filter must be exchanged for every fixed period, whereby it is troublesome.

To cancel this fault, means of opening a plug without generating cut piece by a thin pipe-like needle, such as an injection needle, is also used. With regard to most of the means, the needle serves as a suction nozzle. However, in any case, diameter of the suction nozzle must be small and suction of blood takes a lot of time, thereby constituting a hindrance to rapid analysis.

The plug is not punched out, whereby punched refuse is not generated. However, rounded refuses like those of a rubber eraser are surely generated by friction between the needle and the plug of soft material such as rubber. Since the needle is thin, the needle may be warped when inserted into the plug.

In any case, for making rapid analysis available, it is necessary to keep a measure of size of a diameter of the suction nozzle. Furthermore, for preventing small refuse from being generated, it is preferably to punch out the plug of soft material. Therefore, the purpose of the present invention is to prevent the suction nozzle from sucking punched refuse generated by punching the plug.

BRIEF SUMMARY OF THE INVENTION

An object of the present invention is to provide a method and an implement for opening a hole in soft material so as to prevent a cut piece generated by the opening from being separated out as a refuse from the soft material, thereby especially providing an analyzer such as a hematology analyzer free from the above-mentioned problem.

To achieve the object, a method for opening a hole in soft material according to the present invention comprises a step of cutting a soft material while piercing through the soft material by a hole-opening implement to thereby open a hole in the soft material so that a cut piece as bound to the soft material may remain after the opening, thereby preventing the problem of cut pieces separated from the soft material.

The hole-opening implement has a first cutting part and a second cutting part. The method comprises cutting the soft material by the first cutting part and the second cutting part while the hole-opening implement moves to pierce the soft material, and leaving the second cutting part in the soft material just after the first cutting part is passed through the soft material. By such an easy method, the cut piece as bound to the soft material can remain after the opening.

A plug for sealing a sampling tube serves as the soft material to be opened with a hole therein by the hole-opening implement. A suction nozzle for sucking a sample in the sampling tube is inserted into the tube through the hole opened in the plug. The suction nozzle is prevented from sucking the cut piece separated from the plug and sending it together with the sample to an analyzer or the like.

If the hole-opening implement is tubular, the cut piece remains in the tubular hole-opening implement just after the first cutting part is passed though the soft material. The hole-opening implement is further moved forward so that the second cutting part is passed through the soft material so as to remove the cut piece from the interior of the hole-opening implement, thereby realizing the state that the cut piece is bound to the soft material out of the hole in the soft material opened by the hole-opening implement. In this way, the tubular hole-opening implement makes a hole completely piercing the soft material without the cut piece remaining therein. The cut piece removed from the interior of the hole-opening implement remains as bound to the soft material out of the hole so as not to cause the above-mentioned problem.

When the hole-opening method with the tubular hole-opening implement is used for opening a hole in the soft material provided as a plug for sealing a sampling tube, the tubular hole-opening implement is left in the plug after the opening, and a suction nozzle is passed through the hole-opening implement so as to suck a sample in the sampling tube. Therefore, a labor for removing the hole-opening implement from the plug is saved, and the hole-opening implement remaining in the plug is used as a guide member for guiding the suction nozzle into the sampling tube smoothly, thereby reducing a work time.

In the case of opening a hole in the plug for sealing the sampling tube by the tubular hole-opening implement, the tubular hole-opening implement remaining in the plug may serve as a suction nozzle for sucking a sample in the sampling tube, thereby further reducing a work time and a parts count.

Next, to achieve the above-mentioned object, an implement for opening a hole in a soft material according to the present invention cuts a soft material while piercing through the soft material so that a cut piece as bound to the soft material may remain after the opening.

The hole-opening implement comprises a first cutting part and a second cutting part. The first cutting part and the second cutting part cut the soft material while the hole-opening implement pierces through the soft material, and the second cutting part remains in the soft material just after the first cutting part is passed through the soft material so that the cut piece as bound to the soft material remains after the opening.

A plurality of the second cutting parts may be provided.

In a first aspect of the hole-opening implement having the first cutting part and the second cutting part, the first cutting part has a shape section and the second cutting part may be formed in such a shape that the cutting force thereof is lower than that of the first cutting part.

If the hole-opening implement is tubular, the first cutting part may be formed at an edge of an open tip of the hole-opening implement. By further pushing the tubular hole-opening implement forward in the soft material after the first cutting part is passed through the soft material, the second cutting part having lower cutting force than that of the first cutting part is passed through the soft material so as to push out the cut piece from the interior of the hole-opening implement. Accordingly, the soft material is penetrated by a hole without a cut piece therein. Even if the second cutting part is passed through the soft material, the cut piece removed by the tubular hole-opening implement is not separated from the soft material because of the low cutting force of the second cutting part.

In the case that the hole-opening implement is used for opening a hole in the soft material serving as a plug sealing a sampling tube, the hole-opening implement may be also used as a guide member for guiding a suction nozzle for sucking a sample inserted into the sampling tube. Accordingly, the hole-opening implement need not be pulled outward from the soft material.

Alternatively, in the case that the hole-opening implement is used for opening a hole in the soft material serving as a plug sealing a sampling tube, the hole-opening implement may be left in the plug after the opening so as to be used as a suction nozzle for sucking a sample in the sampling tube. Accordingly, not only the pulling of the hole-opening implement but also insertion of another suction nozzle become unnecessary, thereby reducing a parts count.

The first cutting part having the sharp section and the second cutting part having the lower cutting force may be disposed at substantially the same position in the moving direction of the hole-opening implement for piercing. Even if the first cutting part and the second cutting part are made in this way, the second cutting part can also remain in the soft material just after the first cutting part is passed through the soft material.

In the first cutting part having the high cutting force and the second cutting part having the low cutting force, a surface of the first cutting part may be smooth and a surface of the second cutting part may rough.

If the hole-opening implement is tubular or formed into a solid rod, the first cutting part and the second cutting part disposed at substantially the same position in the moving direction of the hole-opening implement for piercing, or the first cutting part having the smooth surface and the second cutting part having the rough surface may be provided at an outer peripheral edge of a tip of the hole-opening implement.

In a second aspect of the hole-opening implement having the first cutting part and the second cutting part constructed such that, while piercing through the soft material, both the cutting parts move forward into the soft material while cutting the soft material, and the second cutting part remains in the soft material just after the first cutting part is passed through the soft material as mentioned above, the second cutting part is disposed backward from the first cutting part in the piercing direction.

The difference between positions of the cutting parts in the piercing direction realizes that the second cutting part remains in the soft material just after the first cutting part is passed through the soft material. Namely, the positional difference causes a difference between cutting times of the cutting parts.

Such a second cutting part can be made by forming a recess or a notch in the first cutting part backward in the piercing direction.

In the case that the hole-opening implement is shaped into a tube or a solid rod, the first cutting part may be provided at an edge of an open tip of the hole-opening implement. In this case, the second cutting part may be formed into a recess or a notch as the mentioned above. Alternatively, a tip of the hole-opening implement may be slanted from a section perpendicular to the axis thereof so that a forward outer peripheral edge of the tip in the piercing direction serves as the first cutting part, and a backward outer peripheral edge of the tip in the piercing direction serves as the second cutting part. Further alternatively, the second cutting part may be made by notching the backward portion of the swash tip.

The second aspect of construction suggestive of the above-mentioned hole-opening implements can be used in combination with the above-mentioned first aspect of construction of the hole-opening implement. For example, it can be considered that the sharp section of the first cutting part is formed at the edge of the tip of the hole-opening implement formed into a tube or a solid rod and a recess having lower cutting force than that of the first cutting part is formed by notching a portion of the edge of the tip so as to serve as the second cutting part.

The hole-opening implement can be used for opening the soft material serving as a plug sealing a sampling tube so as to introduce a suction nozzle into the sampling tube for sucking a sample in the sampling tube.

In this case, the sampling tube may be a test tube for sampling a medical specimen to be used for a medical analyzer. Furthermore, the medical sampling tube may be a vacuum tube for collecting blood and the medical analyzer may be a hematology analyzer. By using the hole-opening implement of the present invention, an analyzer having a high analytical accuracy free from maintenance for treating the cut pieces generated by the cutting of the plugs can be provided.

These, other and further objects, features and advantages of the invention will appear more fully from the following description taken in connection with the accompanying drawings.

BRIEF DESCRIPTION OF THE DRAWINGS/FIGURES

Figure 4:
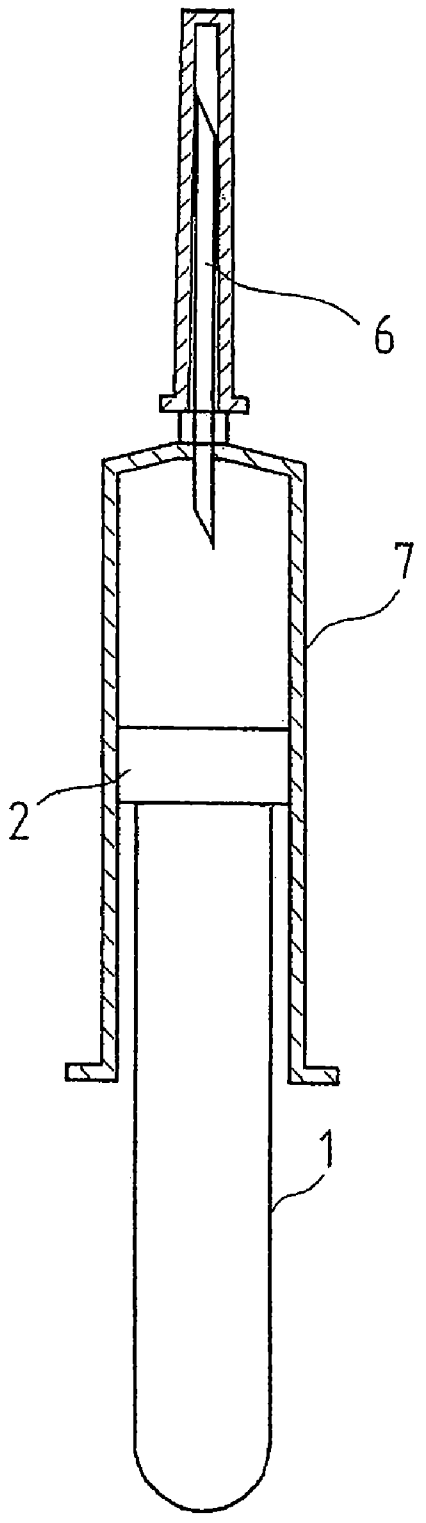

FIG. 4 is a sectional side view showing a state that the vacuum blood-collection tube 1 is inserted into a holder 7 having a multiple-sample blood-collection needle 6.

Figure 5:
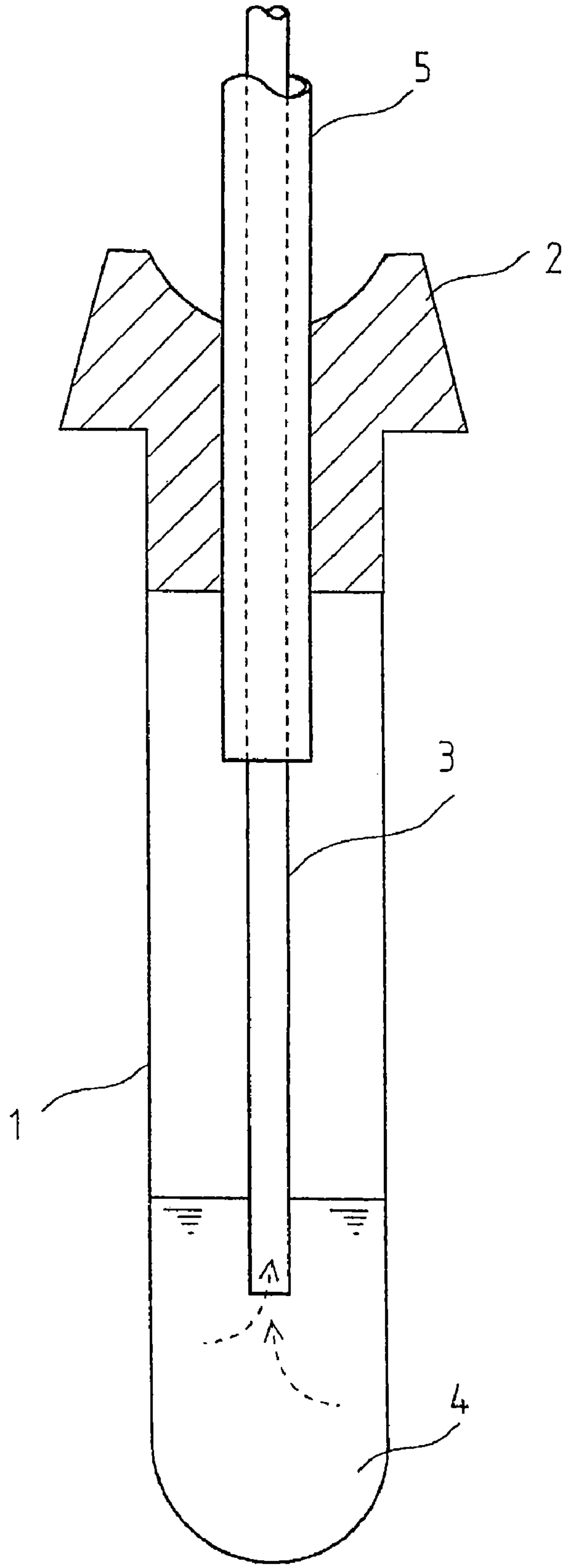

FIG. 5 is a sectional side view showing a state that a suction nozzle 3 is brought into the vacuum blood-collection tube 1 through an hole-opening pipe 5 penetrating the plug 2.

Figure 6:
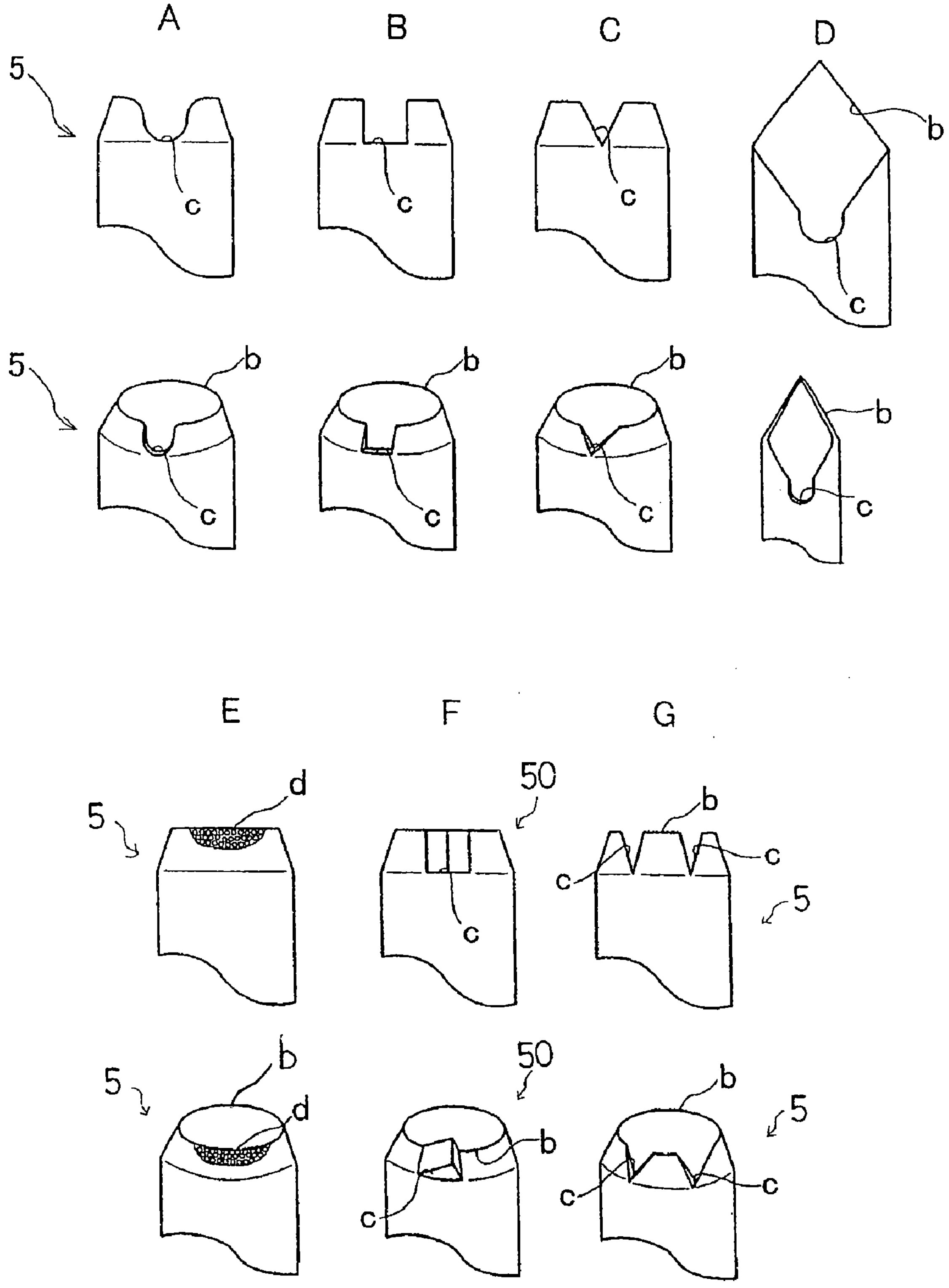

FIG. 6 is a drawing showing side views and perspective views of tips of the opening pipes 5 according to various embodiments A to G of the present invention.

Figure 7:
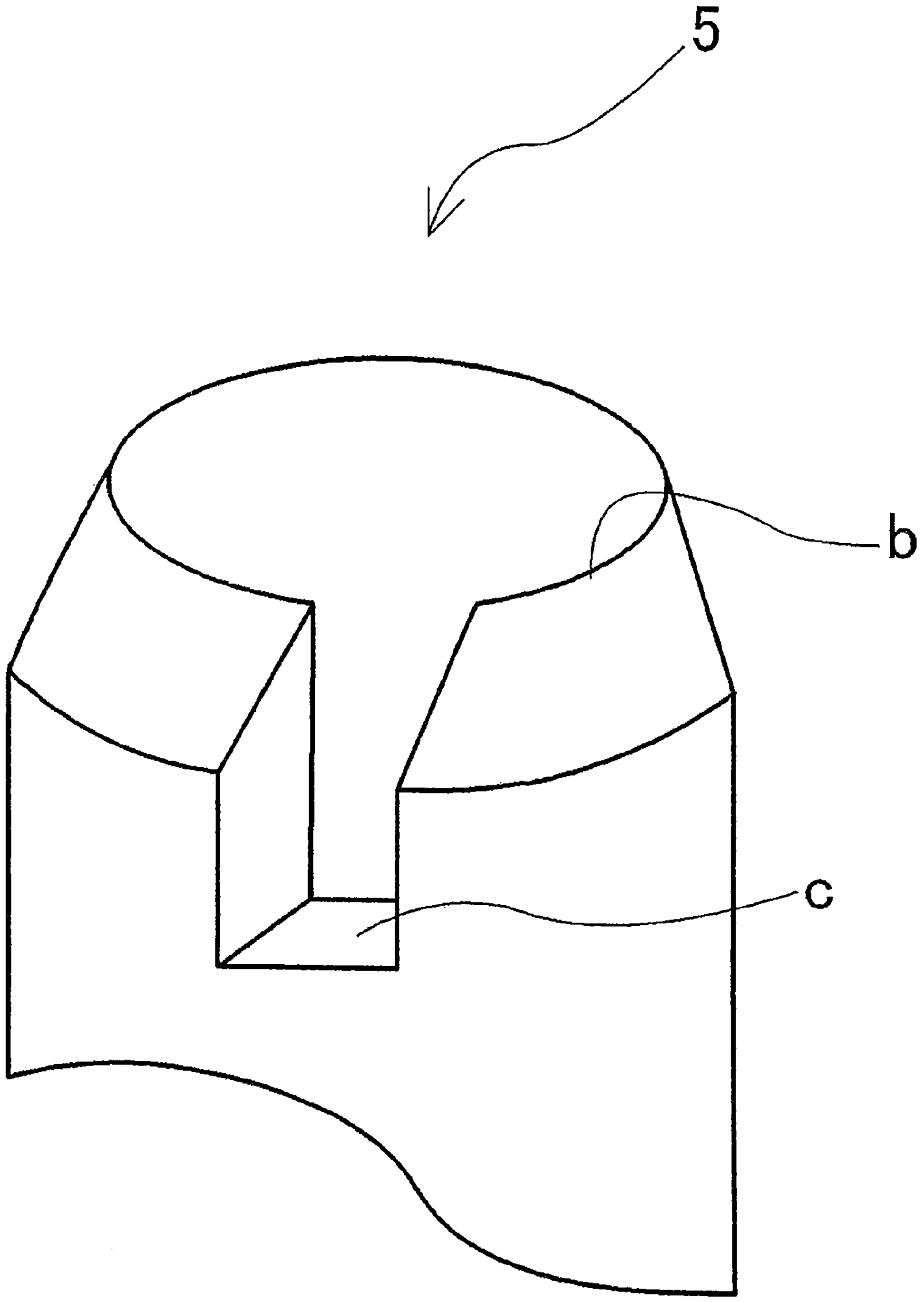

FIG. 7 is a perspective view of the tip of the hole-opening pipe 5 according to the embodiment B in FIG. 6.

Figure 8:
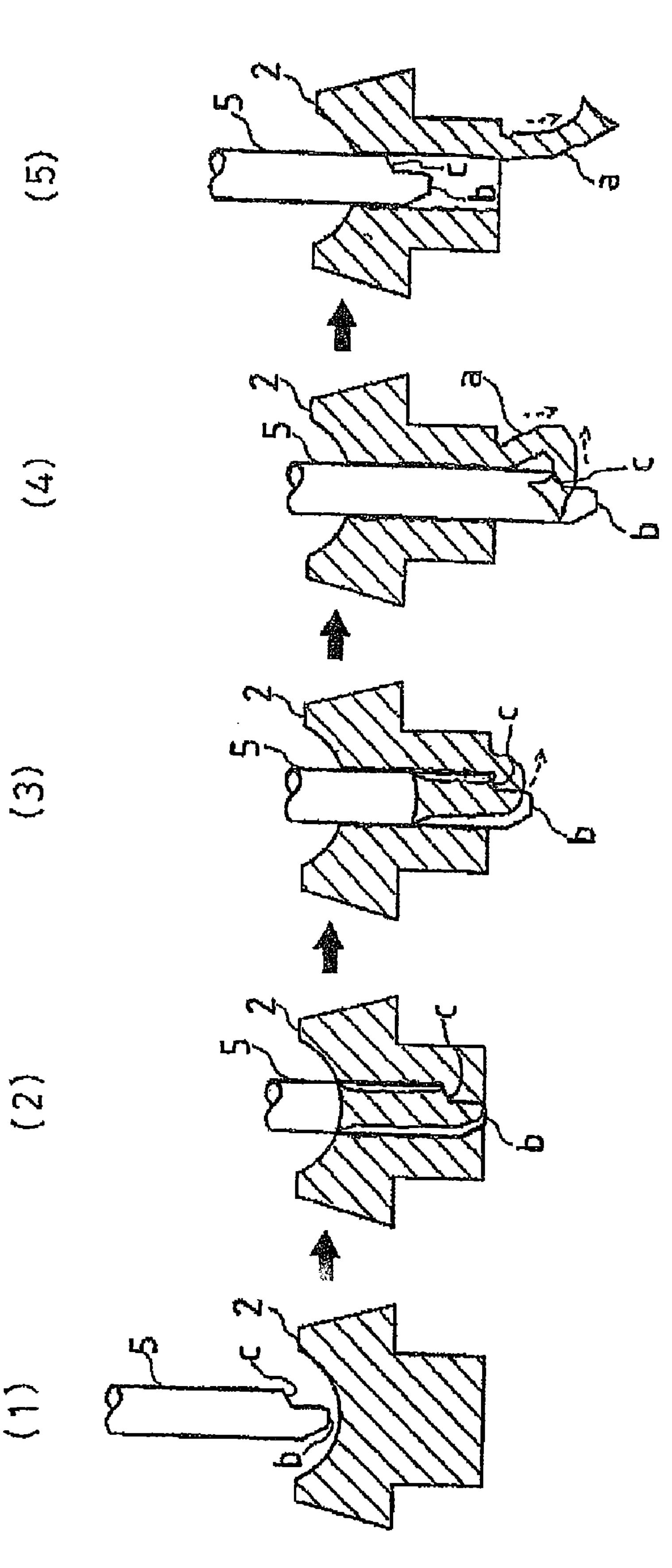

FIG. 8 (1) to (5) are sectional side views of the plug 2 showing the process of opening a hole in the plug 2 by an hole-opening implement, especially by the hole-opening pipe 5 of the embodiment B.

DETAILED DESCRIPTION OF THE INVENTION

Next, explanation will be given of an embodiment of the present invention.

Figure 1:
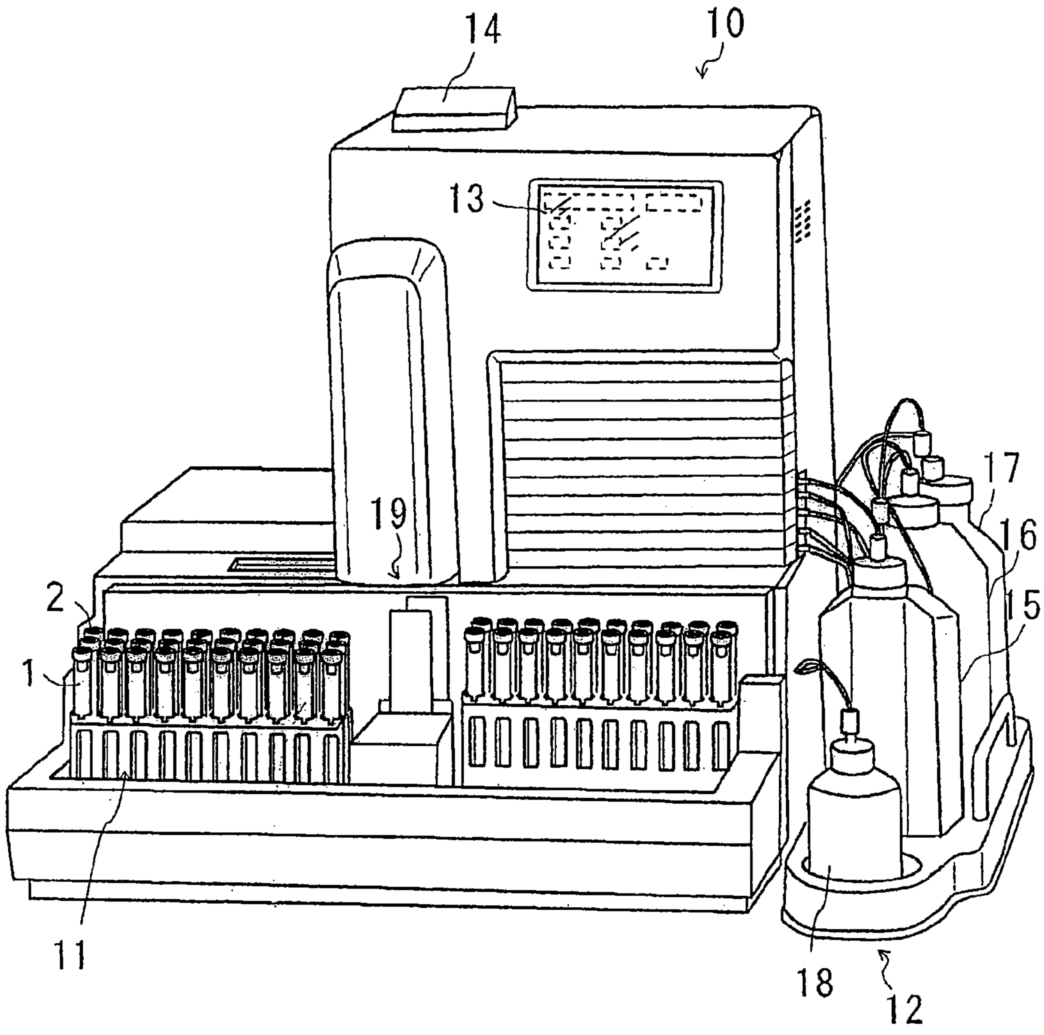
FIG. 1 is an entire perspective view of a fully automatic glucose-measuring device which is one of hematology analyzers and an embodiment of a device to which the present invention is applied.

FIG. 1 is an entire view of a fully automatic glucose-measuring device, which detects the density of glucose in blood by a method of testing whole blood. The glucose-measuring device is an example of a hematological analyzer to which an implement or method of the present invention for opening soft material is applied. This fully automatic glucose-measuring device comprises a main part 10, a sample supply-part 11 and a bottle unit 12.

A print part 14 which prints out each measured value of glucose and a display panel 13 which displays each measured value of glucose on its panel are provided at the main part 10.

Bottles such as a STD liquid bottle 18, a washing liquid bottle 15, a buffer bottle 16 and a waste liquid bottle 17 are disposed in the bottle unit 12.

At the sample supply part 11, a plurality of vacuum blood-collection tubes 1 are set in parallel in a rack. Each vacuum blood-collection tube 1 is continuously conveyed to a nozzle unit 19 provided at a center of the sample supply part 11. When the nozzle unit 19 finishes sampling blood in one of the vacuum blood-collection tubes 1, this vacuum blood-collection tube 1 is taken out and another vacuum blood-collection tube 1 is taken into the nozzle unit 19.

As shown in FIG. 5, in the nozzle unit 19, a plug 2 made of soft material sealing each blood-collection tube 1 is penetrated with an hole-opening pipe 5, and a suction nozzle 3 is inserted into the blood-collection tube 1 through the hole-opening pipe 5, whereby blood 4 which is a specimen in each blood-collection tube 1 is sampled. The present invention relates to construction of an implement for opening a hole in the plug 2, such as the hole-opening pipe 5, and a method of opening a hole in the plug 2 with the hole-opening pipe 5 inserted thereinto.

Figure 2:
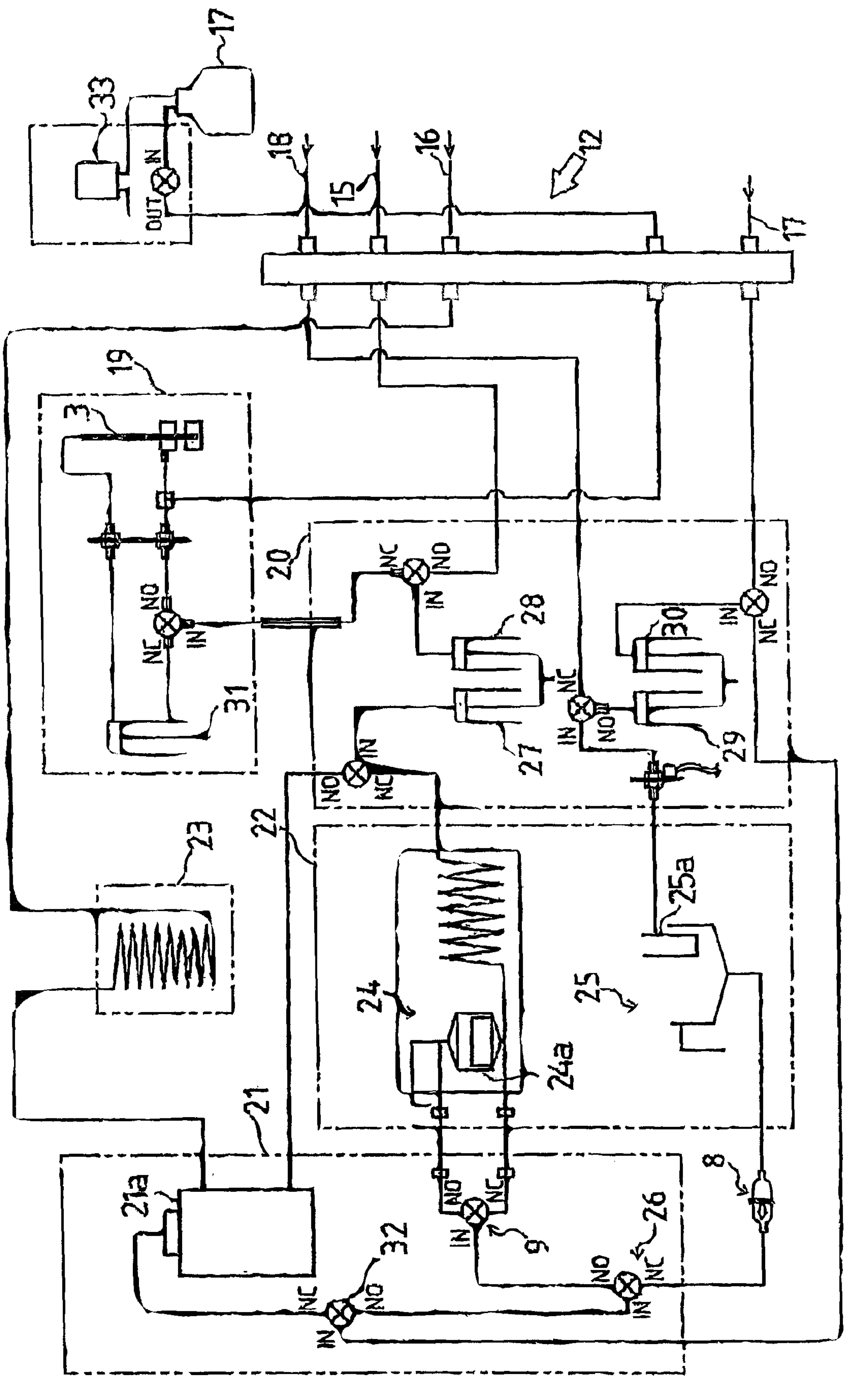
FIG. 2 is a diagram of courses of liquids such as STD liquid, washing liquid, buffer and waste liquid, in the fully automatic glucose-measuring device in FIG. 1.

FIG. 2 shows a schematic construction of the fully automatic glucose-measuring device of FIG. 1. In FIG. 2 are shown liquid-flow paths from the STD liquid bottle 18, the washing liquid bottle 15, the buffer bottle 16 and the waste liquid bottle 17.

The fully automatic glucose-measuring device of this embodiment comprises the bottle unit 12, the nozzle unit 19, a pump chassis 20, a reaction detection part 22 constructed inside the main part 10, a debubbler base 21 in which a debubbler 21*a* is disposed, and a degasser 23.

As mentioned above, the STD liquid bottle 18, the washing liquid bottle 15, the buffer bottle 16 and the waste liquid bottle 17 are disposed in the bottle unit 12, and liquids inside these bottles are supplied to respective parts through various kinds of pumps and valves in the pump chassis 20.

The washing liquid for washing off contaminant of blood adhering to the later-discussed suction nozzle 3 is aqueous solution made by adding low-concentration surface active agent to distilled water or ion-exchanged water. The STD liquid (internal standard liquid for glucose) for automatic calibration of the device is a solution with a certain concentration of glucose. The buffer is provided for reacting GOD immobilizing enzyme with glucose.

Four reciprocating piston type pumps are disposed in the pump chassis 20. A buffer pump 27 sucks and supplies the buffer from the buffer bottle 16. A washing liquid pump 28 supplies the washing liquid from the washing liquid bottle 15 to the suction nozzle 3. A STD liquid pump 29 supplies the STD liquid from the STD liquid bottle 18 to a later-discussed washing tank 25. A waste liquid pump 30 discharges waste liquid after analyzed to the waste liquid bottle 17.

A nozzle pump 31 disposed in the nozzle unit 19 controls the air condition in the suction nozzle 3 inserted into each of the blood-collection tubes 1 so that the suction nozzle 3 sucks blood from the blood-collection tube 1 and drops the blood to a later-discussed reaction tank 24. The nozzle pump 31 also controls the air pressure in the suction nozzle 3 so as to introduce or drain the washing liquid to and from the suction nozzle 3.

The washing liquid introduced into the suction nozzle 3 washes off contaminant of blood from the suction nozzle 3, and then is gathered to the waste liquid bottle 17 by an air pump 33.

On-off solenoid valves are disposed on respective suction and discharge pathways of these pumps 27 to 31. In the drawing, "IN" signifies an entrance of a pipe. "NO" signifies "normally open" and "NC" signifies "normally closed". When required, the "NC" valves are opened for refilling, supplying or discharging. On-off solenoid valves 9, 26 and 32 in the later-discussed debubbler base 21 are the same.

The reaction tank 24 and the washing tank 25 are disposed in the reaction detection part 22. The reaction tank 24 is filled with glucose of the STD liquid or blood, which is diluted with the buffer to a certain concentration. A measuring cell 24*a* including a hydrogen peroxide electrode and a GOD immobilizing enzyme film is disposed in the reaction tank 24 for amperometric detection of glucose in blood. The reaction tank 24 is supplied with the buffer from the buffer bottle 16 through the degasser (gassing apparatus) 23, the debubbler 21*a* (defoaming apparatus) in the debubbler base 21, and an on-off solenoid valve for buffer. The buffer is preheated by the degasser 23 so that oxygen dissolved therein is made into bubble, which is removed from the buffer by the debubbler

21*a*. The STD liquid from the STD bottle 18 is supplied to a STD tank 25*a* in the washing tank 25.

The suction nozzle 3 having sucked blood from the blood-collection tube 1 is sent into the washing tank 25 for washing off waste blood adhering onto an outside of the suction nozzle 3 and removing a refuse caused by a cut piece of the plug 2 (for example, made of rubber) from the blood contaminated with it. The suction nozzle 3 is soaked in the STD tank 25*a* disposed in the washing tank 25 so as to calibrate the concentration of glucose adhering to the outside of the suction nozzle 3. Subsequently, an exactly metered dose of blood sampled by the suction nozzle 3 is supplied as a specimen into the reaction tank 24, the amount of glucose therein is measured by the above-mentioned GOD immobilized enzyme film and hydrogen peroxide electrodes, and the measured result thereof is printed at the print part 14 and displayed by the display panel 13 shown in FIG. 1.

The specimen mixed with the buffer after the reaction in the reaction tank 24 is discharged to the on-off solenoid valve 26 by opening of the on-off solenoid valve 9. Furthermore, waste liquid from the washing tank 25 is discharged to the on-off solenoid valve 26 through a filter 8. The waste liquid discharged by opening the on-off solenoid valve 26 joins waste liquid from the debubbler 21*a* in the on-off solenoid valve 32, and drained by opening the on-off solenoid valve 32.

In such a fully automatic glucose-measuring device, the present invention is applied as a method and an implement for opening a penetrating hole in the plug 2 so as to introduce the suction nozzle 3 into the blood-collection tube 1 set in the nozzle unit 19. The purpose of the present invention is to solve problems. For example, one of the problems is lowering of accuracy of hematological analysis in the analyses tank 24 caused by contamination of the specimen of blood sampled by the suction nozzle 3 with cut pieces generated as refuse at the time of opening the hole in the plug 2. Another is deterioration of function and breakage of the on-off solenoid valves 9 and 26 for passing the waste liquid from the analysis tank 24 because the cut pieces are caught in the valves.

Explanation will be given of a method and an implement for opening a hole in the plug 2 made of soft material according to the present invention with reference to FIGS. 3 to 8.

Figure 3:
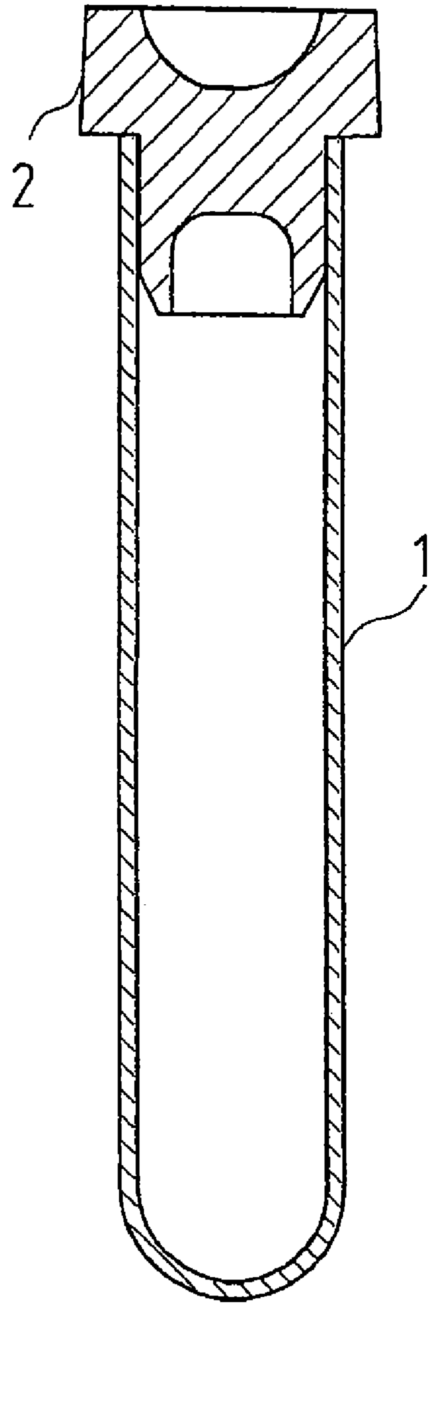
FIG. 3 is a sectional side view of a vacuum blood-collection tube 1 sealed by a plug 2 made of soft material.

As mentioned above, in the sample supply part 11, a plurality of the vacuum blood-collection tubes 1 containing blood 4 (as shown in FIG. 5) and having openings plugged by the respective plugs 2 made of soft material such as rubber as shown in FIG. 3 are juxtaposed as shown in FIG. 1. Materials and forms of the vacuum blood-collection tubes 1 and the plugs 2 made of soft material are prescribed strictly so as to sample blood from the human body.

As shown in FIG. 4, before sampling blood, the vacuum blood-collection tube 1 is inserted into a holder 7 having a multiple-sample blood-collection needle 6 so as to serve as a blood collecting equipment.

At the time of sampling blood 4 from the human body, it is necessary to change an inside of the vacuum blood-collection tube 1 into a predetermined vacuum state corresponding to the amount of blood to be sampled. Therefore, the inside of each vacuum blood-collection tube 1 is changed into the predetermined vacuum state and sealed by the plug 2 so as to keep the vacuum state before the vacuum blood-collection tubes 1 are delivered to a hospital or an inspecting station. A required chemical substance, such as an anticoagulation drug, is supplied in the vacuum blood-collection tube 1 beforehand.

At the time of sampling blood from the human body, firstly, a cover covering the multiple-sample blood-collection needle 6 shown in FIG. 4 is removed and the multiple blood-collection needle 6 is inserted into a blood vessel of an arm of a subject. Next, the vacuum blood-collection tube 1 whose sampling amount of blood is predetermined is inserted into the holder 7 at a rear end of the multiple-sample blood-collection needle 6 while the vacuum blood-collection tube 1 being sealed by the plug 2.

By this operation, the rear end of the multiple-sample blood-collection needle 6 penetrates the plug 2, and the blood 4 from the blood vessel flows into the vacuum blood-collection tube 1 through the multiple-sample blood-collection needle 6. If blood is sampled to two or more vacuum blood-collection tubes 1, the vacuum blood-collection tube 1 with the respective plug 2 is exchanged for another while the multiple-sample blood-collection needle 6 inserted into the blood vessel is kept. The vacuum blood-collection tube 1, which has finished sampling blood in this way, is disposed in the sample supply part 11 of the fully automatic glucose-measuring device as the above mentioned, and blood therein is sucked by the suction nozzle 3 at the nozzle unit 19.

The multiple-sample blood-collection needle 6 passed through the plug 2 for sampling blood comes out of the plug 2 simultaneously with the removal of the vacuum blood-collection tube 1 from the holder 7. However, a hole made by penetration of the multiple-sample blood-collection needle 6 is closed by elastic restoring force of the soft material of the plug 2 after the removal of the multiple-sample blood-collection needle 6, whereby the blood 4 in the vacuum blood-collection tube 1 is kept sealed by the plug 2.

FIG. 5 shows that the hole-opening pipe 5 is inserted into the plug 2 of soft material sealing the vacuum blood-collection tube 1 containing the blood 4 and the suction nozzle 3 is inserted and guided into the vacuum blood-collection tube 1 through the hole-opening pipe 5. The nozzle unit 19 sucks the blood 4 sampled in the vacuum blood-collection tube 1 by the suction pipe 3 set in this way, thereby supplying the blood 4 to the reaction tank 24.

The hole-opening pipe 5 makes a hole having a diameter for insertion and guide of the suction pipe 3 in the plug 2 by punching, namely, cutting the plug 2 in a cylindrical shape. If a columnar cut piece (a punched refuse) generated by the punching is separated from the plug 2, the suction nozzle 3 sucks it together with the blood 4, whereby the refuse adheres to a tip of the suction nozzle 3. If a tip of the hole-opening pipe 5 is shaped like a drill, small refuses disperse and enter the suction nozzle 3, thereby contaminating the blood 4 in the suction nozzle 3. Therefore, the suction nozzle 3 conveys the blood 4 and the punched refuse to the washing tank 25 and the reaction tank 24.

Explanation will be given of problems which may be caused in the reaction tank 24 and the washing tank 25 of the fully automatic glucose-measuring device by suction of the punched refuse by the suction nozzle 3.

With regard to the reaction tank 24, the suction nozzle 3 drops the punched refuse together with the blood 4 thereinto, and the punched refuse is sucked into the reaction tank 24 by the sucking force of the pumps of the pump chassis 20, whereby agitation of the specimen becomes unequal. Additionally, the buffer becomes short by the volume as much as the punched refuse so that the volume of the specimen supplied to the reaction tank 24 does not exactly agree with the predetermined value, whereby the dilution ratio of the blood 4 differs from an optimal value.

In the reaction tank 24, agitation of the specimen may also become unequal under the influence of small refuse chips, which are generated when a hole is opened in the plug 2 by drilling or generated from the above-mentioned punched refuse sucked by the suction nozzle 3, whereby an incorrect value is detected.

Waste liquid from the reaction tank 24 passes the on-off solenoid valves 9 and 26 through upper and lower two passages. At this time, the above-mentioned small refuse chips are pinched between a valve and a valve seat, and so the valve and the valve seat of the solenoid valve are not closed completely. Accordingly, the specimen after reaction may not be discharged well, thereby inhibiting precise analysis.

Even if the refuse chips pass through the on-off solenoid valve 9, a similar problem may occur in the lower on-off solenoid valves 26 and 32.

On the other hand, with regard to the washing tank 25, the punched refuse and the small refuse chips are conveyed to the filter 8 together with contaminant of the specimen, which has adhered to the outside of the suction nozzle 3, and collect on the filter 8. If the refuses are left to collect on the filter 8, washing liquid in the washing tank 25 after washing is not discharged well. In the worst case, the volume of the washing liquid exceeds a predetermined capacity of the washing tank 25 and the liquid overflows therefrom. To avoid this problem, the filter 8 must be exchanged for another predetermined days apart (for example, a few days apart) or on every a certain count of subject.

To solve the above problems, with regard to the nozzle unit 19, a cylindrical hole-opening implement is used so as to open a penetrating hole for guiding the suction nozzle 3 in the plug 2 of soft material without generating small refuse chips and without separating the columnar refuse from the plug 2.

Explanation will be given of embodiments of the hole-opening implement according to FIGS. 6 to 8.

The hole-opening implements are broadly classified into two types: One is for the tubular hole-opening pipe 5 shown in FIG. 5, and the other is for solid opening rods 50 shown in FIG. 6. In the case using the hole-opening pipe 5, the hole-opening pipe 5 is left in the plug 2 after boring so as to serve as a guide, through which the suction nozzle 3 is inserted into the vacuum blood-collection tube 1. In the case using the solid opening rod 50, the opening rod 50 is removed from the plug 2 after boring, whereby the suction nozzle 3 is guided and brought into the vacuum blood-collection tube 1 through a bored hole penetrating the plug 2.

The hole-opening pipe 5 may serve as the suction nozzle 3. Namely, an inside of the hole-opening pipe 5 is connected to the nozzle pump 31, and the hole-opening pipe 5 after piercing the plug 2 is used as a suction nozzle.

In any case, the hole-opening implement of the present invention opens a hole in the plug 2 by neither pushing-and-expanding the plug 2 nor rotary boring like a drill, but by cutting and punching. Accordingly, friction between an peripheral edge of a bored hole and the hole-opening implement, which tend to occur when the hole is opened by pushing-and-expanding the plug 2, is reduced so as to prevent a refuse like that of an eraser caused by the friction. Furthermore, the generation of small refuse chips by the drill-like boring is also prevented.

According to the present invention as an optimal method and structure, a cut piece (punched refuse) a generated at the time of passing of the tubular hole-opening pipe 5 or the solid opening rod 50 through the plug 2 of soft material for opening a hole therein is not separated from the plug 2 of soft material so as to fall into the vacuum blood-collection tube 1, but it is hung down from the plug 2 so as to remain in the vacuum blood-collection tube 1. Example members A, B, C, D, E, F and G shown in FIG. 6 serve as the hole-opening pipe 5 and the opening rod 50.

As shown in FIG. 6, the hole-opening pipe 5 may be a circular cylinder like the examples A, B and C, or alternatively, it may be a square pipe like the member D. If the hole-opening pipe 5 is polygonal in section, the sectional shape may be triangle, pentagon, hexagon or the like other than square.

As shown in each of the examples A to G in FIG. 6, at an outer periphery of a tip of the hole-opening implement concerning the present invention (the hole-opening pipe 5 and the opening rod 50) are formed a first cutting part b, which is so sharp in section as to have high cutting force, and a second cutting part c, which is not so sharp in section as the first cutting part b, i.e., having lower cutting force than the first cutting part b.

With regard to the examples A to D, the second cutting part c is formed backward from the first cutting part b in the movement direction of the hole-opening implement (the hole-opening pipe 5). Namely, the first cutting part b is formed on the outer periphery of the tip of the hole-opening pipe 5, and a slit or a recess is formed backward in the movement direction of the hole-opening pipe 5 from the first cutting part b so as to form the second cutting part c which has a level difference from the first cutting part b.

The second cutting part c of the example A is U-like shaped, that of the example B is square, and that of the example C is V-like shaped. The form of the second cutting part c is not limited to those of the examples. Other various forms are acceptable. The illustrated U-like shape of the second cutting part c in the example D of the square hole-opening pipe 5 may be replaced with another shape such as those of the examples B and C.

In the case of boring the plug 2 by the hole-opening pipe 5 such as any of the examples A to D, the first cutting part b at the tip touches the plug 2 firstly, and cuts into the plug 2 by pushing the hole-opening pipe 5 forward. Then, the second cutting part c touches the plug 2 and cuts thereinto. Namely, cut of the plug 2 by the second cutting part c lags behind that by the first cutting part b. Because of the time lag between cutting by the first cutting part b and cutting by the second cutting part c, the second cutting part c remains in the plug 2 just after the first cutting part b is passed through the plug 2, whereby the punched refuse a as bound to the plug 2 remains after the plug 2 is punched by the hole-opening pipe 5.

The hole-opening pipe 5 is thinner and thinner toward its tip so as to ensure the sharp section of the first cutting part b. The second cutting part c positioned behind the first cutting part b in movement direction of the hole-opening pipe 5 is formed by a thicker portion than the tip, whereby the cutting force of the second cutting part c is lower.

FIG. 7 shows the tip of the hole-opening pipe 5 of the example B, and FIG. 8 (1) to (5) show a series of processes of opening a hole in the plug 2 by the hole-opening pipe 5 of the example B. Explanation will be given of the hole-opening processes and conditions of the punched refuse a as results of the respective processes.

As shown in FIG. 8 (1), when the tip of the hole-opening pipe 5 is brought close to the plug 2, the first cutting part b positioned at the tip touches the plug 2 firstly, and when the hole-opening pipe 5 is pushed further, the first cutting part b cuts into the plug 2 so as to cut the plug 2 substantially cylindrically. The second cutting part c cuts into the plug 2 later than the first cutting part b. The cutting force of the second cutting part c is lower than that of the first cutting part b. However, since a part of the plug 2 touching the second cutting part c has no place to escape in the process that the first cutting part b advances in the plug 2, the pressure of the second cutting part c is effectively applied to the plug 2, whereby the plug 2 is cut by the second cutting part c.

FIG. 8 (2) shows a moment that the first cutting part b finishes cutting the plug 2. At this time, the second cutting part c remains in the plug 2 and has not finished cutting. In the process of pushing the hole-opening pipe 5 so as to project the first cutting part b from the plug 2 into the vacuum blood-collection tube 1 as shown in FIGS. 8 (3) and (4), the punched refuse a is enabled to escape from the inside of the hole-opening pipe 5 to the inside of the vacuum blood-collection tube 1 against the advancing pressure of the second cutting part c. In addition, the second cutting part c having the low cutting force cannot further cut into the plug 2. Therefore, in the process of pushing the hole-opening pipe 5 as shown in FIG. 8 (2) to (4), the second cutting part c does not cut into and cut the plug 2, but only pushes out the substantial cylindrical punched refuse a remaining in the hole-opening pipe 5.

Presently, as shown in FIG. 8 (5), the punched refuse a falls out from the hole-opening pipe 5 completely by pushing of the second cutting part c and hangs down from the plug 2 in the vacuum blood-collection tube 1. Consequently, the punched refuse a as bound to the plug 2 remains.

After this state, the hole-opening pipe 5 may remain in the plug 2 so as to bring the suction pipe 3 into the vacuum blood-collection tube 1 through the hole-opening pipe 5 as shown in FIG. 5. Alternatively, as shown in FIG. 8 (5), the hole-opening pipe 5 may be pulled out from the plug 2 so as to insert the suction pipe 3 through the resulting penetrating hole in the plug 2. Alternatively, the hole-opening pipe 5 may remain in the plug 2 and be used as the suction nozzle 3. In any case, the punched refuse a hanging down from the plug 2 is prevented from being torn off and sucked to the suction pipe 3 by the sucking force of the suction pipe 3, thereby preventing occurrence of the above-mentioned convenient problems in the reaction tank 24, the washing tank 25, and the on-off solenoid valve 9, 26 and 32.

In addition, after sampling of the specimens by the analyzer, the remaining bloods 4 are heated for sterilization and the vacuum blood-collection tubes 1 together with the plugs 2 as medical wastes are incinerated. Therefore, the punched refuses a as cut pieces bound to lower surfaces of the plugs 2 do not cause any problem.

A fully automatic glycohemoglobin-measuring device may be set prior to the fully automatic glucose-measuring device concerning the present invention. Both the devices may be bridge-connected to each other so as to simultaneously analyze the two analysis items. In this case, firstly, the hole-opening pipe 5 opens a hole in the plug 2 for the fully automatic glycohemoglobin-measuring device, and then, the vacuum blood-collection tube 1 is moved to the fully automatic glucose-measuring device so as to have another hole in the plug 2 opened by the hole-opening pipe 5 of the fully automatic glucose-measuring device. By opening the two holes in the plug 2 by the hole-opening pipes 5 of the respective devices according to the present invention, the punched refuses a caused by the respective openings are prevented from being separated from the plug 2 and remain hanging down from the plug 2.

In a usual case of supplying the vacuum blood-collection tube 1 to both nozzle units 19 of the fully automatic glucose-measuring device and the full automatic glycohemoglobin-measuring device by the same sample supply part 11, the respective positions of the plug 2 against the hole-opening pipes 5 of the nozzle units 19 are shifted from each other by rocking the rack of the sample supply part 11 or the like so as to prevent the hole-opening pipe 5 of the second device of the two from being inserted into the hole previously opened by the hole-opening pipe 5 of the first device. However, even if the respective positions of the plug 2 against the hole-opening pipes 5 become the same, the hole-opening pipe 5 of the second device does not touch a punched refuse a hanging down from the plug 2 as a result of opening by the hole-opening pipe 5 of the first device, whereby the hole-opening pipe 5 of the second device does not separate the punched refuse a from the plug 2. By setting a common portion in the plug 2 into touch with the second cutting parts c of both of the hole-opening pipes 5, the hole-opening pipe 5 of the second device surely prevents the separation of the punched refuse a.

Each example of the hole-opening implement shown in FIG. 6 will be described again.

With regard to the example D as the sectionally square hole-opening pipe 5, the tip thereof is cut aslant so as to form a square section which has a corner at the extremity thereof so as to serve as the first cutting part b having enhanced sharpness and cutting force.

With regard to the examples A to C, the tip of the hole-opening pipe 5 formed in a circular cylinder may be cut aslant similarly. In this case, a front portion of the tip in the piercing direction is defined as the first cutting part b, and a rear portion thereof as the second cutting part c. The rear portion may be cut so as to form the second cutting part c similar to the example D.

With regard to the example E in FIG. 6, the second cutting part d is formed on the outer periphery of the extremity of the hole-opening pipe 5 together with the first cutting part b. Namely, the first cutting part b and the second cutting part d are formed at the same position in the movement direction of the hole-opening pipe 5, whereby the timing and depth of cutting the plug 2 by them are equalized. An edge of the first cutting part b is smoothed and that of the second cutting part d is made uneven, whereby the cutting force of the second cutting part d is lower than that of the first cutting part b.

At the time of opening of the plug 2 by the example E of the hole-opening pipe 5, since the second cutting part d has an ability of cutting the plug 2 less than the first cutting part b, the second cutting part d does not finish cutting the plug 2 at the time that the first cutting part b finishes cutting the plug 2 as shown in FIG. 8 (2). Even if the hole-opening pipe 5 is pushed further forward, the second cutting part d cannot cut the plug 2 and only pushes out the punched refuse a remaining in the hole-opening pipe 5 as shown in (3) and (4) of FIG. 8. Therefore, finally, similarly to the above-mentioned examples A to C of the hole-opening pipe 5 having the second cutting part c behind the first cutting part b in the movement direction, the hole-opening pipe 5 leaves the punched refuse a as hung down from the plug 2, as shown in FIG. 8 (5).

With regard to the example F in FIG. 6, the first cutting part b is formed on the outer peripheral of the tip of the solid hole-opening rod 50, and the second cutting part c having a level difference from the first cutting part b is formed by cutting the tip thereof. In the case of opening a hole in the plug 2 by this solid hole-opening rod 50, the second cutting part c does not finish cutting the plug 2 and remains therein at the time that the first cutting part b finishes cutting the plug 2, whereby the punched refuse a as hung down from the plug 2 remains similarly.

With regard to the solid hole-opening rod 50, the second cutting part c may be formed in various forms as those of the examples A to C of the hole-opening pipe 5. Alternatively, the second cutting part c may be formed at the extremity of the hole-opening rod 50 similarly to the first cutting part b as shown in the example E. The hole-opening rod 50 may be either circular or polygonal (tetragon or another) in section.

Furthermore, as shown in the example G in FIG. 6, the hole-opening implement may be provided with two or more second cutting parts c. The example G of the hole-opening pipe 5 is formed with two V-like shaped second cutting parts c. The second cutting parts c are not limited in form to those of the example. The second cutting parts c may be formed at the extremity of the hole-opening implement similarly to the first cutting part b in the example E. The number of the second cutting parts c is not limited to two. The solid opening rod 50 may be also formed with two or more second cutting parts c.

The examples A to D in FIG. 6 are constructed so as to leave the punched refuse a as bound to the plug 2 by the synergism of the difference of cutting time between the first cutting part b and the second cutting part c with the difference of cutting force therebetween. Alternatively, the section of the second cutting part c may be shaped similar to the first cutting part b so as to have equal cutting force. In this case, the first cutting part b serving as a first cutting part and the second cutting part c serving as a second cutting part, the punched refuse a is prevented from being separated from the plug 2 by only the difference of cutting time between the first and second cutting parts. Also in this case, the cutting implement is moved out from the plug 2 in the direction opposite to the vacuum blood-collection tube 1 (upward in FIG. 8) at the state that the first cutting part b finishes cutting the plug 2 and the second cutting part c remains in the plug 2, thereby preventing the second cutting part c from cutting off the punched refuse a from the plug 2.

INDUSTRIAL APPLICABILITY

The foregoing description about holding of a hole in a plug made of soft material such as rubber provided in a vacuum blood-collection tube is a preferred embodiment of application of the invention. Alternatively, the present invention may be applied to other medical sampling containers, such as a urine-collection tube. The present invention contributes for providing an analyzer, which is useful and has high analytical accuracy because it requires no maintenance for treatment of cut pieces generated from the plug. Further alternatively, the present invention is applicable to opening a hole for insertion of a suction tube in a cap, lid or rubber plug of a PET bottle, laminated tube or paper pack for containing drink or other liquid. Further, the present invention is utilizable for various uses requiring opening of a hole.

What is claimed is:

1. A method for opening a hole in a plug made of soft material, the plug sealing a sampling tube, by use of a tubular hole-opening implement having a first cutting part, a second cutting part and a longitudinal axis, said method comprising the steps of:

piercing the plug with the hole-opening implement;

moving the hole-opening implement towards the sampling tube in the direction of the longitudinal axis so as to cut the plug with the first cutting part and the second cutting part;

passing the first cutting part through the plug, wherein the second cutting part remains in the plug so as to leave a cut piece, having been a part of the plug, inside the hole-opening implement so that the cut piece remains bound to the plug after the first cutting part is passed through the plug;

further moving the hole-opening implement towards the sampling tube in the direction of the longitudinal axis so as to pass the second cutting part through the plug, thereby removing the cut piece from the inside of the hole-opening implement and thereby forming a hole through the plug, so that the cut piece remaining bound to the plug is disposed outward from the hole; and inserting a suction nozzle into the hole so as to suck a sample in the sampling tube, wherein the hole-opening implement has a peripheral tip edge disposed perpendicular to the piercing direction of the hole-opening implement so as to constitute the first cutting part, the piercing direction being parallel to the longitudinal axis of the hole-opening implement.

2. The method for opening a hole in the plug as set forth in claim 1, further comprising a step of:

moving the hole-opening implement in the direction of the longitudinal axis away from the sampling tube after the removal of the cut piece from the inside of the hole-opening implement so as to remove the hole-opening implement from the plug, wherein the suction nozzle is inserted into the hole through the plug after the removal of the hole-opening implement from the plug.

3. The method for opening a hole in the plug as set forth in claim 1, wherein the tubular hole-opening implement is left in the plug after the removal of the cut piece from the inside of the hole-opening implement, and wherein the suction nozzle is inserted into the hole-opening implement left in the plug, thereby being inserted into the hole.

4. The method for opening a hole in the plug as set forth in claim 1, wherein the tubular hole-opening implement is left in the plug after the removal of the cut piece from the inside of the hole-opening implement so as to serve as the suction nozzle inserted into the hole.

* * * * *